United States Patent [19]

Fabri et al.

[11] Patent Number: 6,149,822
[45] Date of Patent: Nov. 21, 2000

[54] BIO-FILM CONTROL

[75] Inventors: Jon O. Fabri, Charleston, S.C.; Walter D. Heslep, Madison, Mich.

[73] Assignee: Polymer Ventures, Inc., Charleston, S.C.

[21] Appl. No.: 09/260,377

[22] Filed: Mar. 1, 1999

[51] Int. Cl.⁷ .................................................. C02F 1/50
[52] U.S. Cl. .......................... 210/764; 162/161; 422/16; 422/28; 514/580; 514/588; 514/634; 514/666; 514/697
[58] Field of Search ............................ 162/161; 210/749, 210/764; 422/28, 16; 514/513, 580, 588, 592, 634, 666, 697

[56] References Cited

U.S. PATENT DOCUMENTS

| | | |
|---|---|---|
| T965,001 | 12/1977 | Carbone et al. . |
| 2,428,329 | 9/1947 | Ham et al. ............................. 204/180 |
| 2,884,395 | 4/1959 | Wohnsiedler . |
| 3,166,471 | 1/1965 | Gump . |
| 3,223,513 | 12/1965 | Geary . |
| 3,231,509 | 1/1966 | Shema . |
| 3,957,904 | 5/1976 | Isaoka et al. . |
| 4,025,429 | 5/1977 | Neuschütz . |
| 4,026,796 | 5/1977 | Wegmüller et al. . |
| 4,097,376 | 6/1978 | Wegmuller et al. . |
| 4,271,028 | 6/1981 | Marfurt et al. . |
| 4,380,602 | 4/1983 | Dumas . |
| 4,380,603 | 4/1983 | Bankert . |
| 4,382,129 | 5/1983 | Bankert . |
| 4,383,077 | 5/1983 | Bankert . |
| 4,439,290 | 3/1984 | Marfurt et al. . |
| 4,479,820 | 10/1984 | Merk et al. ............................. 162/161 |
| 4,673,509 | 6/1987 | Davis et al. . |
| 4,690,765 | 9/1987 | Linder et al. . |
| 4,690,766 | 9/1987 | Linder et al. . |
| 4,720,345 | 1/1988 | Linder et al. . |
| 4,767,645 | 8/1988 | Linder et al. . |
| 4,857,209 | 8/1989 | Lyons et al. . |
| 4,902,779 | 2/1990 | Waldmann . |
| 4,976,874 | 12/1990 | Gannon et al. . |
| 4,995,944 | 2/1991 | Aston et al. . |
| 5,032,282 | 7/1991 | Linder et al. . |
| 5,047,144 | 9/1991 | Dobias et al. . |
| 5,049,282 | 9/1991 | Linder et al. . |
| 5,169,536 | 12/1992 | Vasconellos et al. . |
| 5,300,194 | 4/1994 | Welkener et al. . |
| 5,302,291 | 4/1994 | Miknevich . |
| 5,362,842 | 11/1994 | Graves et al. . |
| 5,368,694 | 11/1994 | Rohlf et al. . |
| 5,707,532 | 1/1998 | Guerro et al. . |
| 5,866,016 | 2/1999 | Jaquess et al. . |
| 5,888,405 | 3/1999 | McNeel et al. ......................... 210/764 |

*Primary Examiner*—Peter A. Hruskoci
*Attorney, Agent, or Firm*—Dority & Manning, P.A.

[57] ABSTRACT

A process is provided for both removing and controlling biofilms present in industrial cooling and process waters. The process provides a composition which includes the reaction products of an amino base, a formaldehyde, an alkylenepolyamine, and the ammonium salt of an inorganic or organic acid. The composition may be used to remove existing biofilms from process water equipment. Further, lower maintenance dosages may be used to maintain the equipment in a substantially biofilm-free condition.

10 Claims, No Drawings

BIO-FILM CONTROL

BACKGROUND OF THE INVENTION

The present invention generally relates to a method for reducing biofilm coatings and similar organic deposits in water systems. More particularly, the present invention is directed to an amine-formaldehyde condensate, optionally blended with surfactants in order to provide a composition useful as a biodispersant in cooling water systems. The composition can be used for preventing slime masses which result from bacterial, fungal, or algal growth. The elimination of such growth maintains water contact surfaces in a growth-free state and results in improved heat transfer efficiency of the equipment. In addition, water re-circulation lines, pumps, and reservoirs associated with the cooling equipment are maintained in a growth free state. The reduction in biofilm deposits also helps in the control of scale and corrosion. Further benefits include more effective control of pathogenic organisms such as Legionella pneumophila, which has caused outbreaks of Legionnaire's disease attributed to contaminated water cooling systems. The products of this invention will generally be used in conjunction with oxidizing and/or non-oxidizing biocides to affect a microbial control treatment regimen.

In the past, others have attempted to suppress biofilm growth and production from cooling water systems. For instance, U.S. Pat. No. 4,673,509 to Davis et al., which is incorporated herein by reference, discloses a method for treating water systems which are susceptible to biofilm growth. In Davis et al., hydroxy alkyl phosphorus compounds are used to control aquatic growth and films in process water systems. U.S. Pat. No. 4,976,874 to Gannon et al., incorporated herein by reference, discloses a method and formulation for the control of biofouling using an oxidizing halogen in combination with a non-oxidizing quaternary ammonium halide. U.S. Pat. No. 5,866,016 to Jacquess et al., incorporated herein by reference, teaches a method for controlling biofouling with a combination of ionene polymers with salts of dodecylamine, where the ionenes are classified as quaternary ammonium polymers.

As will be clear from the description which follows, there remains room for improvement and variation within the art.

In general, the present invention is directed to a process for the control of biological and other organic containing deposits in industrial cooling and process waters. Very generally, the composition of the present invention relates to materials that, when applied to cooling waters, remove biofilms and control their growth. At higher concentrations, the material provides a successful treatment formulation for existing contamination, followed by subsequent control through lower maintenance doses.

SUMMARY OF THE INVENTION

The present invention recognizes and addresses the problems associated with the control of biofilms and biological growth within industrial cooling and waste water. Accordingly, it is an object of the present invention to provide a biofilm control composition. It is another object of the present invention to provide a method of controlling the formation of biofilms in industrial cooling and process water systems. It is yet a further object of this invention to limit the surface attachment of microorganisms, which leads to the biofilms on surfaces of water system equipment. Another object of the present invention is to provide a biofilm control composition and method that is compatible with existing chemical treatments for corrosion inhibition, scale and mineral deposits, as well as with biocides, both oxidizing and non-oxidizing.

These and other objects of the present invention are achieved by providing a composition for removing and preventing biofilms in industrial cooling and process water systems. The composition includes an amine-formaldehyde condensate optionally with a surfactant. The inclusion of from about 0.1% to about 10% of a surfactant to the amine-formaldehyde condensate also provides a highly effective composition which has been found useful for the control of aqueous bacterial, algal, and fungal deposits.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction.

The present invention is directed to a composition and method for the control of biofilms. As used herein, the term biofilm refers to organic films and deposited matter resulting from metabolic activity of biological organisms. Control of the biofilms means the prevention or substantial reduction of biofilm formation. The term "control" also refers to the ability to slow the development of a biofilm by the use of the present invention, compared to a system or application without the present invention. As used herein, the term "control" also includes treatments designed to eliminate or substantially reduce established biofilms. Once treated, the present invention is further capable of controlling additional biofilm formation through maintenance protocols as established herein.

More specifically, an amine-formaldehyde condensate made from 1–95% by weight of amine selected from the group comprising dicyandiamide, guanamines, guanidine, melamine, aniline, urea, thiourea, cyanamide, and guanylurea, combinations and salts or derivatives thereof; 0–20% by weight of an alkylenepolyamine selected from alkylamines, alkyldiamines, alkenepolyamines, alkanolamines, and combinations thereof; 1–98% by weight of an inorganic or organic acid, optionally neutralized with ammonium hydroxide or alkali; 1–98% by weight of formaldehyde or its precursors/donors; and 0–10% by weight of a surfactant is an effective composition. Aminopolymers such as those referenced above constitute a well-known class of compounds as described in *Organic Polymer Chemistry*, 2nd ed., Chapman and Hall, 1988, pp. 341–357, and incorporated herein by reference.

More specifically, the amine-formaldehyde condensates which are most effective are the reaction product of an amino base, a formaldehyde, an alkylenepolyamine, and the ammonium salt of an inorganic or organic acid. Condensates of this type are well known and are described in U.S. Pat. Nos. 3,106,541, 3,410,649, 3,582,461, and 4,383,077, the disclosures of which are incorporated herein by reference. Exemplary amino bases are dicyandiamide, guanamines, guanidine, melamine, aniline, urea, thiourea, cyanamide, guanylurea, and combinations thereof.

The formaldehyde component may be obtained from aqueous solutions or in polymeric or bound form such as paraformaldehyde, trioxane, hexamethylenetetramine, an acetal, or other formaldehyde donor.

The alkylenepolyamine is selected from the group comprising ethylenediamine, propylenediamine, butylenediamine, pentylenediamine, hexamethylenediamine, diethylenetriamine, triethylenetetramine, tetraethylenepentamine, 1,2- propylenediamine, dibutylenetriamine, tributylenetetramine, tetrabutylenepentamine, dipentylenetriamine, tripentylenetetramine, tetrapentylenepentamine, alkanolamines, and combination isomers, oligomers, or polymers thereof.

The ammonium salts of acids may be formed prior to introduction to the other reagents or formed in situ by reacting the corresponding acid such as hydrochloric, sulfuric, phosphoric, boric, formic, acetic, glycolic, propionic, butyric, and the like with ammonium hydroxide or ammonia.

Optionally, a cationic and/or nonionic surfactant may be blended or reacted with the condensate polymer described above. The surfactant may contain low levels of anionic groups but are predominantly cationic or nonionic in charge. The cationic surfactant is preferably a quaternary ammonium halide compound, and more preferably an alkyldimethylbenzyl-ammonium chloride wherein the alkyl group consists of between 8 and 22 carbon atoms (Barquat, Lonza, Inc.). The nonionic surfactants include condensation products of ethylene oxide and/or propylene oxide with hydrophobic materials such as fatty alcohols or alkylphenols (Tergitol, Union Carbide), and ethylene oxide copolymers with propylene oxide (Pluronic, BASF).

The reactions described above were used with the materials listed in the following product examples to provide the biocidal compositions. The biocidal compositions were then used as described in the working examples which follow. The following examples and embodiments are intended to illustrate, not limit, the invention.

Product Examples
Amine-Formaldehyde Condensates Formulations

| Example Product #1 | Example Product #5 |
|---|---|
| Dicyandiamide | Dicyandiamide |
| Ammonium Chloride | Melamine |
| Formaldehyde | Ammonium Chloride |
|  | Formaldehyde |
| Example Product #2 | Example Product #6 |
| Dicyandiamide | Dicyandiamide |
| Urea | Ammonium Chloride |
| Ammonium Chloride | Formaldehyde |
| Formaldehyde | Monoethanolamine |
| Example Product #3 | Example Product #7 |
| Dicyandiamide | Example Product #1 |
| Ammonium Chloride | Tergitol 12S3 |
| Formaldehyde |  |
| Diethylenetriamine |  |
| Example Product #4 | Example Product #8 |
| Dicyandiamide | Example Product #3 |
| Hexamethylenetetramine | Barquat MB50 |
| Formic Acid |  |
| Ammonium Hydroxide |  |

APPLICATION EXAMPLES

Example A

An open recirculating cooling water system is used to control the temperature of fermentation tanks. The water circulates through coils and jackets in the tank, over an induced draft cooling tower, then back to the sump from which it is pumped. Because of contamination with bacteria and highly nutritive substances from the surrounding environment, microorganisms flourish in the cooling water system. This results in biofilms building on heat transfer surfaces and on the cooling tower water distribution and support components, resulting in poor cooling efficiency.

The system was treated several times per week with alternating dosages of non-oxidizing and oxidizing biocides. Due to the severity of the biofouling, several different treatment regimens were tried in an attempt to improve the 3 F°ΔT caused by the biofilm build-up. None were successful at economically feasible dosages.

100 ppm (based on system water holding capacity) of the Example Product #6 was slug fed to the system. After 1 day, the visible biofilm on the cooling tower began to diminish. After 2 days, the ΔT improved to 5 F°. After 3 days, almost all visible biofilm had disappeared, foaming had ceased, and the ΔT had improved to 7 F°. The improvement in the ΔT resulted from the removal of biofilm from both the fermentation tank heat exchange surfaces, as indicated by monitoring inbound and outbound water temperatures, and from the removal of biological growth and deposits from the cooling tower water distribution structures. The system is being maintained in this condition by twice-per-week 100 ppm doses of Example Product #6 and twice-per-week doses of a non-oxidizing biocide.

Example B

A hospital air conditioning condenser is served by an open-deck cooling tower located on the roof. The cooling tower deck and fill require cleaning every four to six weeks during the summer. The system is treated two to four times per week with a non-oxidizing biocide. Example Product #3 was slug fed at a dosage of 200 ppm based on the water holding capacity of the system. Three days later, all algae and bacteria slime had disappeared. Slug dosages of 50 ppm of Example Product #3 followed by a slug dose of non-oxidizing biocide five to ten hours later maintain this system in a biofilm-biodeposit free condition.

Example C

Three identical roof top cooling tower systems on the same industrial plant were treated with equal dosages of biodispersants. The bacteria counts were determined on water samples taken at 2, 5, 24 hours after a slug dosage of 50 ppm actives was added to the cooling systems.

| System No. | Product | 0 hrs. | 2 hrs. | 5 hrs. | 24 hrs. |
|---|---|---|---|---|---|
| 1 | Ex. Product #1 | 32875 | 20005 | 38672 | 8511 |
| 2 | Mayquat TC-76 | 30472 | 14395 | 13895 | 18226 |
| 3 | Buckman WSCP | 28128 | 18398 | 30160 | 24230 |

This data indicates that Example Product #1 dispersed aerobic bacteria better than the other biodispersants tested, as indicated by the bacteria counts at 5 hours. The counts at 24 hours show that the dispersed bacteria have a mortality rate that is directly related to the effectiveness of the biodispersant.

Example D

Laboratory tests were conducted on water samples collected from a river flowing through a highly industrialized region. The samples were treated, plated on nutrient agar, incubated for 24 hours at 35°–37° C. and counted for total aerobic bacteria.

The results were:

| Product | Dosage | Count |
|---|---|---|
| 1.5% Isothiazolin | Blank | 14,600 |
|  | 30 ppm | 15,900 |
|  | 60 ppm | 14,000 |
|  | 120 ppm | 15,500 |
| 0.9% Isothiazolin and | Blank | 14,300 |
| 20% Ex. Product #1 | 30 ppm | 10,500 |
|  | 60 ppm | 13,500 |
|  | 120 ppm | 6,300 |
| 10% DBNPA | Blank | 17,000 |
|  | 20 ppm | 5,100 |
|  | 40 ppm | 3,700 |
|  | 100 ppm | 1,800 |
| 10% DBNPA and | Blank | 16,000 |
| 20% Ex. Product #2 | 20 ppm | 2,700 |
|  | 30 ppm | 3,000 |
|  | 50 ppm | 1,000 |

The addition of Example Products #1 and #2 to water in conjunction with well-known non-oxidizing biocides improved the performance of these biocides.

As set forth above and in reference to the examples, the present invention provides a useful composition and process for controlling biofilms in industrial cooling and process water systems. The present invention effectively controls biofilm formation and growth, is operative over a wide range of temperature and pH, is compatible with conventional equipment, and has a sufficient range of chemical compositions such that a compatible formulation may be customized to the operating conditions.

The composition and process of the present invention is useful within industrial cooling equipment and certain process water systems, including holding tanks, conduits, and other distribution equipment.

The present invention also has applications for uses where maintenance treatment levels are not possible, though periodic biofilm treatment is needed. For instance, the present invention allows agricultural irrigation or waste lagoon lines to be periodically treated for biofilm accumulation as well as equipment associated with water treatment and distribution.

These and other modifications and variations to the present invention may be practiced by those of ordinary skill in the art without departing from the spirit and scope of the present invention, which is more particularly set forth in the appended claims. In addition, it should be understood that aspects of the various embodiments may be interchanged in whole or in part. Furthermore, those of ordinary skill in the art will appreciate that the forgoing description is by way of example only and is not intended to limit the invention so further described in such appended claims.

That which is claimed:

1. A process of controlling biofilms in aqueous systems comprising adding an effective amount of an amine-formaldehyde condensate composition to the aqueous system, wherein said amine-formaldehyde condensate composition is made with an amine or corresponding salt selected from the group consisting of dicyandiamide, guanamines, guanidine, melamine, aniline, urea, thiourea, cyanamide, guanylurea, derivatives thereof, and combinations thereof, and an ammonium salt of an inorganic or organic acid.

2. The process according to claim 1 wherein said amine-formaldehyde condensate composition is further made with a polyamine selected from the group comprising of alkylenepolyamines, alkanolamines, alkylamines, alkyldiamines, and combinations thereof.

3. The process according to claim 1 wherein said amine-formaldehyde condensate composition is made with mineral or organic acid, and combinations thereof.

4. The process according to claim 1 wherein said amine-formaldehyde condensate composition is made with a formaldehyde selected from the group comprising of an aqueous formaldehyde solution, a polymeric formaldehyde, and a bound formaldehyde.

5. The process according to claim 1 wherein said composition comprises a dicyandiamide-formaldehyde condensate.

6. The process according to claim 1 wherein said composition further comprises between 0.1 to 10% by weight of a nonionic surfactant.

7. The process according to claim 1 wherein said composition further comprises between 0.1 to 10% by weight of a cationic surfactant.

8. A process of controlling biofilms in an aqueous system comprising:

providing a biofilm inhibiting composition of an aqueous polymer amine-formaldehyde condensate made from:

1–95% by weight of an amine selected from the group consisting of dicyandiamide, guanamines, guanidine, melamine, aniline, urea, thiourea, cyanamide, guanylurea, derivatives thereof, and combinations thereof; and effective amount of an ammonium salt of an inorganic or organic acid;

0–20% by weight of a polyamine;

1–98% by weight of an acid; and,

0–10% by weight of a surfactant;

contacting a surface having a biofilm with a treatment solution comprising an effective amount of said composition;

maintaining said contacting step for an effective time interval, thereby dispersing said biofilm.

9. The process according to claim 8 wherein said process comprises the additional steps of:

maintaining an effective amount of said composition within an operating liquid of said aqueous system, thereby preventing the generation of a biofilm.

10. The process according to claim 8 wherein the step of providing a composition further comprises providing a composition having a corrosion inhibitor.

* * * * *

UNITED STATES PATENT AND TRADEMARK OFFICE
CERTIFICATE OF CORRECTION

PATENT NO : 6,149,822
DATED : Nov. 21, 2000
INVENTOR(S): Jon O. Fabri and Walter D. Heslep It is certified that error appears in the above-identified patent and that said Letters Patent is hereby corrected as shown below:

IN THE ADDRESS OF INVENTOR HESLEP:

Please delete [Michigan] and replace with Mississippi

Signed and Sealed this

First Day of May, 2001

Attest:

NICHOLAS P. GODICI

*Attesting Officer*    *Acting Director of the United States Patent and Trademark Office*